United States Patent
Hara et al.

(10) Patent No.: US 6,792,132 B1
(45) Date of Patent: Sep. 14, 2004

(54) INSPECTION METHOD FOR MICROORGANISMS AND THE LIKE, AND UNIT THEREFOR

(75) Inventors: Akikuni Hara, Tokyo (JP); Toshimitsu Asano, Kashiwa (JP); Yoshiaki Torai, Sapporo (JP); Akihiro Omi, Sapporo (JP)

(73) Assignee: Hakuju Institute For Health Science Co., Ltd., Tokyo (JP)

( * ) Notice: Subject to any disclaimer, the term of this patent is extended or adjusted under 35 U.S.C. 154(b) by 0 days.

(21) Appl. No.: 09/601,507

(22) PCT Filed: Feb. 2, 1999

(86) PCT No.: PCT/JP99/00429

§ 371 (c)(1),
(2), (4) Date: Aug. 2, 2000

(87) PCT Pub. No.: WO99/40176

PCT Pub. Date: Aug. 12, 1999

(30) Foreign Application Priority Data

Feb. 3, 1998 (JP) .......................................... 10-036827
Nov. 10, 1998 (JP) .......................................... 10-334931

(51) Int. Cl.⁷ .............................. G06K 9/00; C12Q 1/04
(52) U.S. Cl. ...................... 382/110; 382/128; 382/133; 382/162; 382/165; 435/34; 436/20; 702/21
(58) Field of Search .................................. 382/110, 128, 382/170, 162, 165, 168, 133; 435/31–40; 702/21, 28; 436/20–24

(56) References Cited

U.S. PATENT DOCUMENTS

| | | | | |
|---|---|---|---|---|
| 4,207,554 A | * | 6/1980 | Resnick et al. | 382/133 |
| 4,591,554 A | * | 5/1986 | Koumura et al. | 435/18 |
| 4,885,697 A | * | 12/1989 | Hubner | 702/27 |
| 5,290,701 A | * | 3/1994 | Wilkins | 435/287.3 |
| 5,356,793 A | * | 10/1994 | Koezuka et al. | 435/32 |
| 5,428,690 A | * | 6/1995 | Bacus et al. | 382/128 |
| 5,473,706 A | * | 12/1995 | Bacus et al. | 382/133 |
| 5,510,246 A | * | 4/1996 | Morgan | 435/39 |
| 5,526,258 A | * | 6/1996 | Bacus | 382/129 |
| 5,579,409 A | * | 11/1996 | Vaidyanathan et al. | 382/203 |
| 5,694,478 A | * | 12/1997 | Braier et al. | 382/133 |
| 5,766,868 A | * | 6/1998 | Seto | 435/8 |
| 5,783,411 A | * | 7/1998 | Schisler et al. | 435/34 |
| 5,861,270 A | * | 1/1999 | Nelis | 435/34 |
| 6,327,377 B1 | * | 12/2001 | Rutenberg et al. | 382/133 |
| 6,461,833 B1 | * | 10/2002 | Wilson | 435/34 |
| 6,485,962 B1 | * | 11/2002 | Tabacco et al. | 435/288.7 |
| 6,546,123 B1 | * | 4/2003 | McLaren et al. | 382/128 |

* cited by examiner

Primary Examiner—Bhavesh M. Mehta
Assistant Examiner—Aaron Carter
(74) Attorney, Agent, or Firm—Stites & Harbison PLLC; B. Aaron Schulman

(57) ABSTRACT

A method and an apparatus for inspecting microbes, etc. including, as an apparatus for detecting microbes, etc., a cultivating device, an image taking-in device, and an arithmetic processing unit, in which an image of a medium to be inspected obtained from a sample collected from a substance or a physical solid having proper color microbes or the medium subjected to illumination treatment, dyeing treatment, etc. prior to or after cultivation in accordance with necessity is separated into the three primary colors, or the like, then, chromatic information of histogram, color and hue for each primary color are calculated, and the information thus obtained is compared with integrated data obtained by combining second data of generic information of microbes, etc. with first data of microbes, etc. which are preliminarily accumulated in the same procedure as the above, so that the features specific to microbes are extracted for identification of the kind of the microbes, and a state of propagation of the microbes after the passage of a predetermined time is anticipated, thereby a state of propagation of the microbes after the passage of a predetermined time required for cultivation of microbes in the medium can preliminarily be detected make anticipate in a short time.

15 Claims, 13 Drawing Sheets

(a)

(b)

INSPECTION METHOD FOR MICROORGANISMS AND THE LIKE, AND UNIT THEREFOR

TECHNICAL FIELD

This invention relates to a method and an apparatus for inspecting (i.e., detecting and/or identifying) bacteria and other microbes.

BACKGROUND OF THE INVENTION

With respect to food (all kinds of food including meat, sea product such as fish, etc.) to be put on the market, it is customary that the material for such food is preliminarily processed into a predetermined condition in a factory and then brought into market. In the factory, the processed food is inspected as to whether it is contaminated with pathogenic bacteria and other microbes. In a typical conventional method for detecting microbes, etc. contained in food, target microbes are picked up from a sample and cultivated in an incubator for a prescribed time, so that the cultivated microbes can visually be measured and detected. To carry out this correctly, however, a special technique accompanied with a long time experience is required.

Recently, a method using a computer was proposed. In this proposal, an image of a medium to be inspected, taken into a computer is binalized to calculate a determining level for inspection. However, this method is encountered with such a problem that even slight differences in angle of illumination, direction, etc. of a light source with respect to the medium can immediately adversely affect a correct determination of the medium because the image is instantaneously binalized when it is taken into the computer. Consequently, the result of inspection is varied, thus providing an inaccurate inspection result.

Furthermore, since the correct determining level cannot be obtained, it is difficult to carry out a correct inspection under the present circumstance. Moreover, there is involved in the convention method such an additional problem that even if food is contaminated with microbes in one way or others (i.e., mere attachment to the food, potential presence in the food, generation in the food) which could later be hazardous to human, most of such pathogenic microbes do not show their actual figure until after the passage of a predetermined time. For this reason, it often happens that after the food processed in a factory is carried out for delivery, pathogenic microbes are propagated and when the food is delivered to consumers, those who eat the food are suffered from food poisoning.

Moreover, the conventional techniques for inspecting microbes required long time for obtaining a result of inspection. However, recently, owing to improvement of the inspecting techniques such as the direct observing method through a microscope, the membrane dyeing method, the electrical impedance method, the fluorescent dyeing method, the fluorescent probing method, the bioluminescence measuring method, etc. which are employed for inspecting microbes present in processing food, semi-processed food, processed food, etc., a rapid inspection could somehow be obtained. However, even those improved inspecting techniques have many advantages and shortcomings in respect of rapidity, the range of inspection, economic efficiency, etc. and are still far from complete satisfaction. In some of the inspecting techniques, a specific microbe can be identified but actually, in most of them, it is difficult to identify microbes.

It is, therefore, an object of the present invention to provide a method and an apparatus for inspecting a medium such as microbes, etc., in which an image of a medium cultivated in a short time (about 5 to 6 hours) are separated, for example, into the three primary colors and then, histogram, color and hue are calculated, so that a growth efficiency for anticipating the growth of a colony of microbes and a feature efficiency for determining the features specific to each microbe are established, then, the data preliminarily calculated in the same procedure as the above and accumulated are searched and compared for identification, and then a state of propagation of those microbes after the passage of time (24 hrs., 48 hrs, etc.) generally required for cultivating the microbes utilizing the growth efficiency, etc. is anticipated, thereby a state of propagation of the microbes after the passage of a predetermined time can easily be known in advance in spite of short time.

Another object of the present invention is to provide a method and an apparatus for inspecting a medium such as microbes, etc., in which the degree of accuracy for identifying microbes is enhanced, an image of such microbes is correctly determined and photographed, and devices for inspecting a medium are housed in a case as one group, thereby not only determination of the medium and accumulation of the result of inspection can be made automatically but also the bacteria in the medium can be reduced in number and sterilized easily.

DISCLOSURE OF THE INVENTION

According to the present invention, there is provided a method and an apparatus for inspecting microbes, etc., characterized in that in order to preliminarily know a state of propagation, for example, of bacteria (respiring bacteria) after the passage of a predetermined time, an image of a medium obtained from a foodstuff such as food including drinking water and a processed material is separated into the three primary colors in a computer, histogram, hue and color are calculated for each primary color and compared with data of each kind of bacteria preliminarily accumulated according to the above-mentioned procedure so that the features specific to the bacteria are extracted for identification and an anticipated state of propagation of the bacteria after the passage of a predetermined time is calculated, so that a state required for propagation of the identified bacteria after the passage of a predetermined time can preliminarily be detected make anticipate in a short time.

From another aspect of the present invention, there is also provided a method for inspecting microbes, etc., in which an image of a medium to be inspected collected from foodstuff such as food including drinking water and a processed material thereof is separated into the three primary colors, then, chromatic information of histogram, color and hue for each primary color are calculated, and the information thus obtained is compared with integrated data obtained by combining second data of generic information of microbes, etc. with first data of microbes, etc. which are preliminarily accumulated in the same procedure as the above, so that the features specific to microbes are extracted for identification of the kind of the microbes, and a state of propagation of the microbes after the passage of a predetermined time is anticipated, thereby a state of propagation of the microbes after the passage of a predetermined time required for cultivation of microbes in the medium can preliminarily be detected make anticipate in a short time. Also, there is a provision of provision of a phtographing device for accurately photogrphing an image of microbes by preliminarily subjecting the medium to dyeing treatment and light emitting treatment, where necessary. Also, there is a further provision of an inspecting device, in which related devices are housed in a casing as one group in order to inspect the medium, thereby not only determination of the medium and accumulation of the result of inspection can be made automatically but also the bacteria in the medium can be reduced in number and sterilized.

BEST MODE FOR CARRYING OUT THE INVENTION

Figure 1:
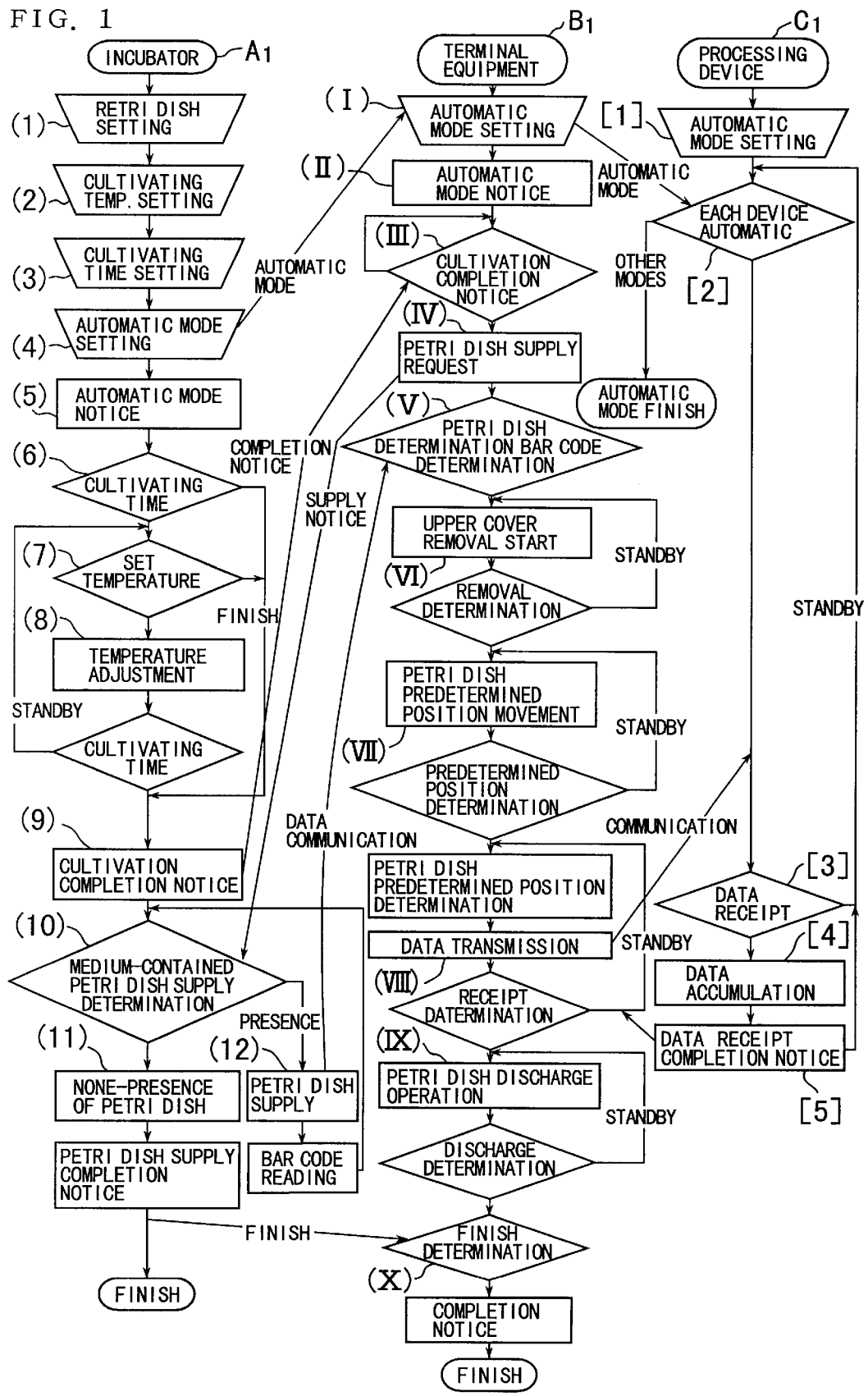
FIG. 1 is a flowchart showing an apparatus and a method for inspecting microbes, etc., according to the present invention.

One embodiment of the present invention will now be described with reference to the accompanied drawings. FIG. 1 is a flowchart showing an apparatus and a method for inspecting microbes, etc., according to the present invention. In FIG. 1, (1) to (12) show a construction and operation of a cultivating device [incubator] ($A_1$). The construction and operation of the cultivating device will be described hereinafter in sequential order. In the step of (1), a culture medium (agar) inoculated with bacteria (the culture medium inoculated with bacteria is hereinafter referred to as the "medium". In case this medium is in a liquefied state, a filter is used to collect the bacteria. The medium may take many other forms) is put into a petri dish ($1a$) and then set in the incubator ($A_1$). In the step of (2), the cultivating temperature is set. The cultivating temperature is set to a required level by appropriately operating an operation panel of the incubator ($A_1$). In the step of (3), the cultivating time is set. Also in this case, the time required is set by appropriately operating the operation panel. In the step of (4), the operation panel of the incubator ($A_1$) is operated to realize an automatic operation mode [this is operatively connected to a terminal equipment ($B_1$) and a processing device ($C_1$) as later described].

Then, in the step of (5), the automatic operation mode (a manual operation mode may be employed, where necessary, when it is desired to cultivate bacteria for 24 hours, 48 hours, for example) is informed to the terminal equipment ($B_1$). In the cultivating time in the step of (6), the automatic mode cultivating time setting in the step of (3) is determined. In the set temperature in the step of (7), it is determined whether the temperature is the cultivating temperature set in the step of (2). In temperature adjustment in the step of (8), when the temperature is not in the range of the set temperature, a control is made for the prevention of an occurrence of over-heating. In the notice of completion of cultivation in the step of (9), the completion of cultivation is informed to both the terminal equipment ($B_1$) and the processing device ($C_1$). In the medium-contained petri dish supply determination in the step of (10), it is determined whether or not a request for supply the medium-contained petri dish ($1a$) is made by the terminal equipment ($B_1$). In the notice of none-presence of the medium-contained petri dish/finishment in the step of (11), the none-presence of the medium-contained petri dish ($1a$) is informed to the terminal equipment ($B_1$) and the automatic mode is finished. In the medium-contained petri dish supply/next bar code reading in the step of (12), the medium-contained petri dish ($1a$) is supplied to the terminal equipment ($B_1$) and a bar code is given thereto for reading.

(I) to (X) show the construction and operation of the terminal equipment ($B_1$). The construction and operation thereof will be described hereinafter in sequential order. In the automatic mode setting in the step of (I), the operation panel of the terminal equipment ($B_1$) is operated to realize an automatic mode [this is operatively connected to the incubator ($A_1$) and a processing device ($C_1$) as later described. In the automatic mode notice in the step of (II), the automatic mode is informed to both the incubator ($A_1$) and the processing device ($C_1$). In the cultivation completion notice in the step of (III), the terminal equipment ($B_1$) standbys until the arrival of the cultivation completion notice from the incubator ($A_1$) and informs it only after its arrival. In the medium-contained petri dish supply request in the step of (IV), a request for the medium-contained petri dish is sent to the incubator ($A_1$). In the medium-contained petri dish determination bar code determination in the step of (V), it is determined that the medium-contained petri dish ($1a$) is set in a predetermined position and the bar code is read. In the cover removal in the step of (VI), an upper cover of the medium-contained petri dish ($1a$) is removed. In the medium-contained petri dish predetermined position determination in the step of (VII), it is determined that the medium-contained petri dish ($1a$) is set in a predetermined position within the terminal equipment ($B_1$). In the data transmittance in the step of (VIII), it is determined whether or not an image of the medium set in a predetermined position is received in a normal condition. In the medium-contained petri dish discharging operation in the step of (IX), the medium-contained petri dish (1a) is discharged or accumulated outside the terminal equipment (B₁). In the finishment determination in the step of (X), it is determined whether or not the none-presence of the medium-contained petri dish (1a) is informed from the incubator (A₁) and if the result of determination is affirmative, a finishment notice is sent to the processing device (C₁).

[1] to [5] show the construction and operation of the processing device (C₁). The construction and operation thereof will be described hereinafter in sequential order. In the step of [1], an automatic mode is set. The operation panel of the processing device (C₁) is operated to realize an automatic mode [this is operatively connected to the incubator (A₁) and a processing device (C₁) as later described]. [2] shows automatic determination of each device. Here, it is determined whether or not both the incubator (A₁) and the terminal equipment (B₁) are set to the automatic mode. [3] shows the data receipt. Here, the processing device (C₁) receives an image of the medium transmitted from the terminal equipment (B₁) and accumulates it inside thereof. When accumulated in a normal condition, a normal receipt signal is output to the terminal equipment (B₁). [4] shows data accumulation and [5] shows data receipt completion notice.

Here, the data of an image of the medium transmitted to the data receipt in the step of [5] of the processing device (C₁) from the data transmittance in the step of (VIII) of the terminal equipment (B₁) are image processed within a computer. That is, the image is expressed in three bytes and separated by logical operation of each byte. Then, by calculating histogram, hue and color for each data item separated, the feature of the microbes is extracted. The features are expressed in coefficient. Then, by searching the preliminarily prepared data base (data obtained by analyzing and orderly arranging the data accumulated), the kind of the bacteria of the medium is identified. Furthermore, based on the searched data, an anticipation of growth of the bacteria is made. By this, cultivation, measurement of the kind and number of the colony of microbes can be made in a short time.

Figure 2:
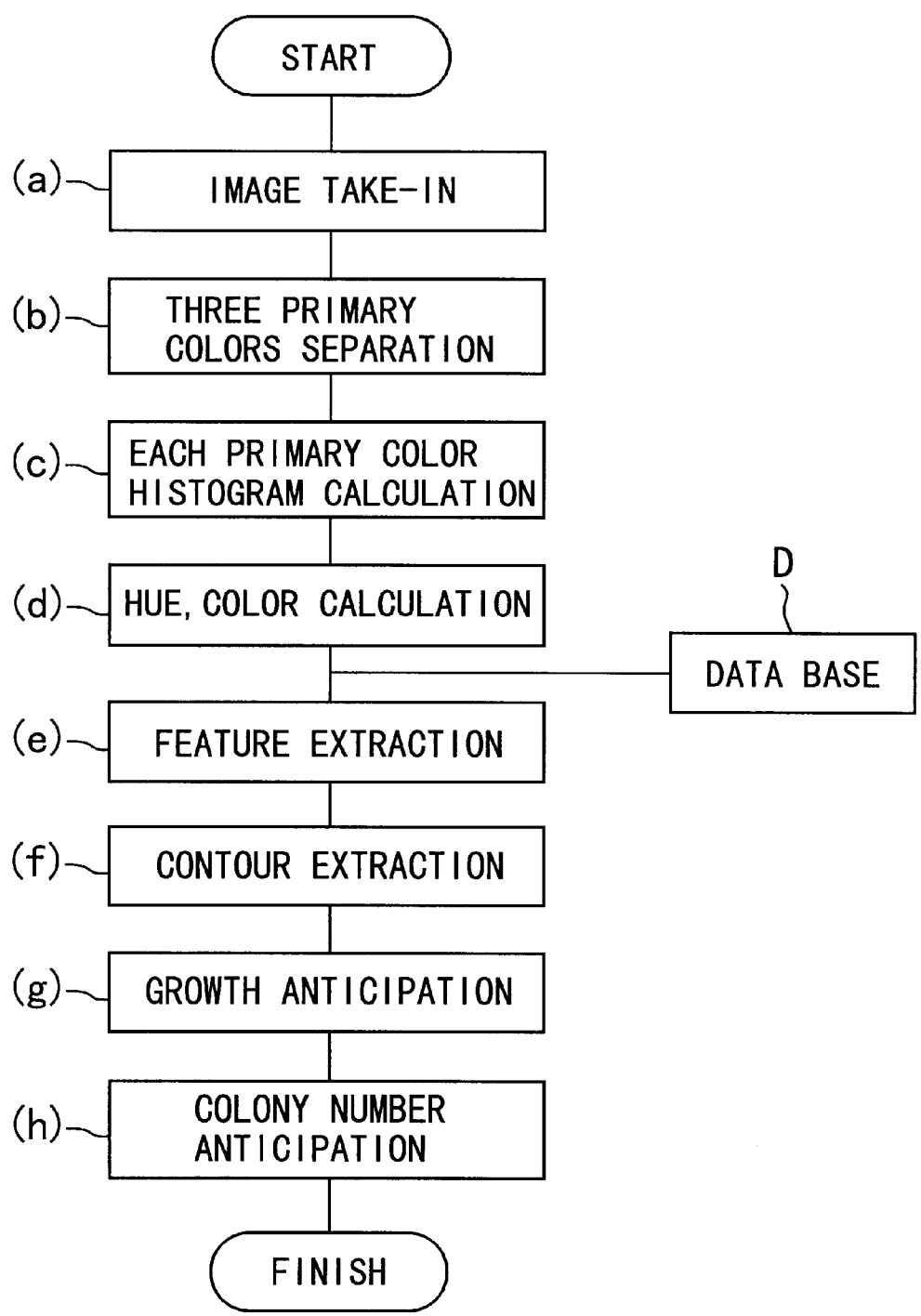
FIG. 2 is a flowchart showing the procedures for taking in, extracting and anticipating the growth of an image of microbes, etc., according to the present invention.

A sequence of processing operation within the computer previously mentioned will now be described in more detail. In the flowchart of FIG. 2, after starting the operation, an image having proper color is taken into the computer in the step of (a) [this procedure will be described in greater detail later], and the image thus taken into the computer is separated, for example, into the three primary colors, red R, green G and blue B at (b). Then, in the step of (c), histogram of each primary color is calculated and dissolved into density distribution of 256 kinds of colors, and in the step of (d), hue and color are calculated, in other words, kinds of the colors and density are established. For feature extraction in the step of (e), a comparison is made with the data base (D) to thereby establish the kind of the microbes. That is, the new data obtained from the image just processed are compared with the data base (D) [as a construction of the data base, ID, kinds of bacteria (group/individual, for example, coliform bacilli), feature coefficient (R, G, B distribution <histogram value>, H, S distribution <hue, color values>) are prepared in the same procedure as above and preliminarily taken in] to extract the features of the kinds of bacteria, thereby the kinds of bacteria are identified.

Figure 3:
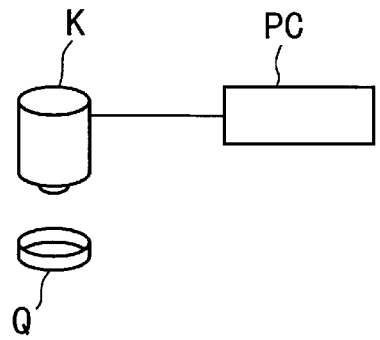
FIG. 3 is an explanatory view showing an essential portion of the apparatus according to the present invention.
Figure 4:
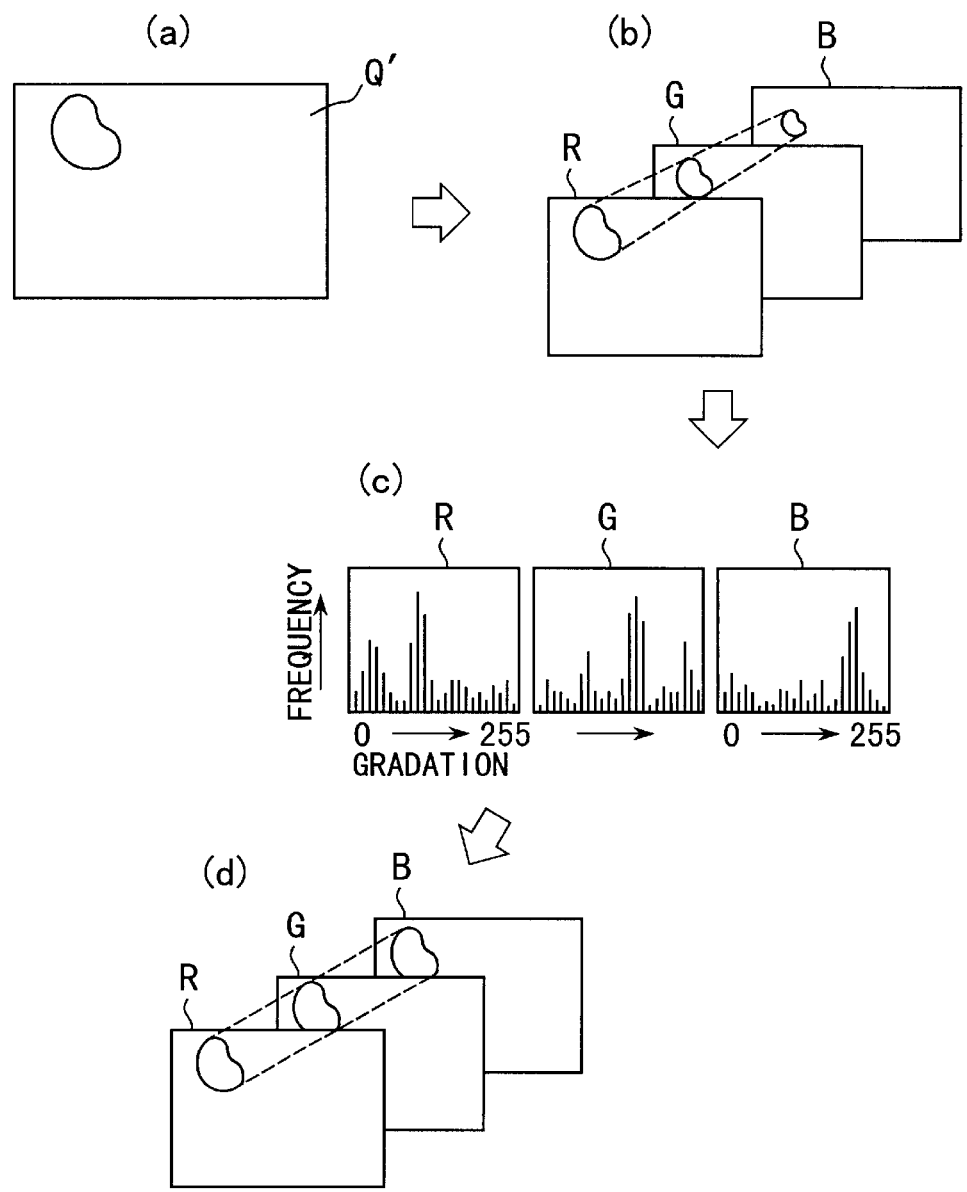
FIG. 4 is a view for explaining the development of transformation of an image of a medium to be inspected, according to the present invention.

Then, in the step of (f), a contour of the colony is extracted from the data thus read. In the step of (g), growth of the colony is anticipated and in the step of (h), the number of colonies of bacteria is anticipated. Here, the contour of the colony is extracted based on the data thus read and a growth degree α (as later described) is calculated based on a distance between respective contours and area of the colony) in order to make an anticipation such as, for example, 24 hours, 48 hours based on the growth degree α thus obtained. This procedure will be described in more detail with reference to the drawings [FIGS. 3, 4(a) to 4(d), and 5(a) to 5(d)]. First, one example of an image taking-in procedure of FIG. 2(a) will be described with reference to FIG. 3. As an image reading device of FIG. 3, a CCD camera (k) is used to take an image (Q') of the medium (Q) (see FIG. 4) cultivated for a predetermined time, into a computer (PC).

That is, on the stage where the image (Q') is separated into the three primary colors as in the step of (b) shown in FIG. 2, the medium image (Q') is expressed in three bytes of R, G and B and stored in the memory within the computer (PC). This image is expressed in the form of a multiple value image (color image: an image where each pixel has not only gradations but also colors) and separated into three primary colors (basic values of color expression) using the following equation for calculating histogram (that is, gradation, i.e., density is calculated for each primary color).

$$\sum_{n=0}^{255} F(N) = FR(n) \cap R_1$$

[where: N is the number of brightness, FR is brightness at the detected spot, n is brightness at the inspected spot, and ∩ is a logical product]

In this separating method, the primary three colors R, G and B, for example, are superimposed to provide a color expression. Here, in the color image data, each primary color is expressed by a number of three figures. By this, a logical arithmetic calculation is made for each primary color and the image is separated for each primary color [see FIG. 4(b)]. Then, on the stage for calculating the histogram for each primary color in the step of (c) of FIG. 2, the density distribution is calculated for each R, G, B as shown in the graph of FIG. 4(c). Then, in FIG. 4(d), hue and color are calculated in accordance with the following equations.

$$S = S_r + S_g + S_b$$

$$S_r = 255 - R + \beta$$

$$= \frac{255}{R + G + (G + B - 2R)} + \beta$$

$$S_g = 255 - G + \beta$$

$$= \frac{255}{R + G + (B + R - 2G)} + \beta$$

$$S_b = 255 - B + \beta$$

$$= \frac{255}{R + G + (R + G - 2B)} + \beta$$

$$H = \frac{255 \times \theta}{2\pi}$$

$$\theta = \frac{2R - G - B}{\sqrt{8(R - 85)^2 + (G + 85)^2 + (B + 85)^2}}$$

In the calculation of hue and color, color S and hue H are calculated using the above hue color equations. In the above equations, Sr is a hue element of the R color, Sg is a hue element of the G color and Sb is a color element of the B color. β is a coefficient specific to make clear of the image.

Figure 5:
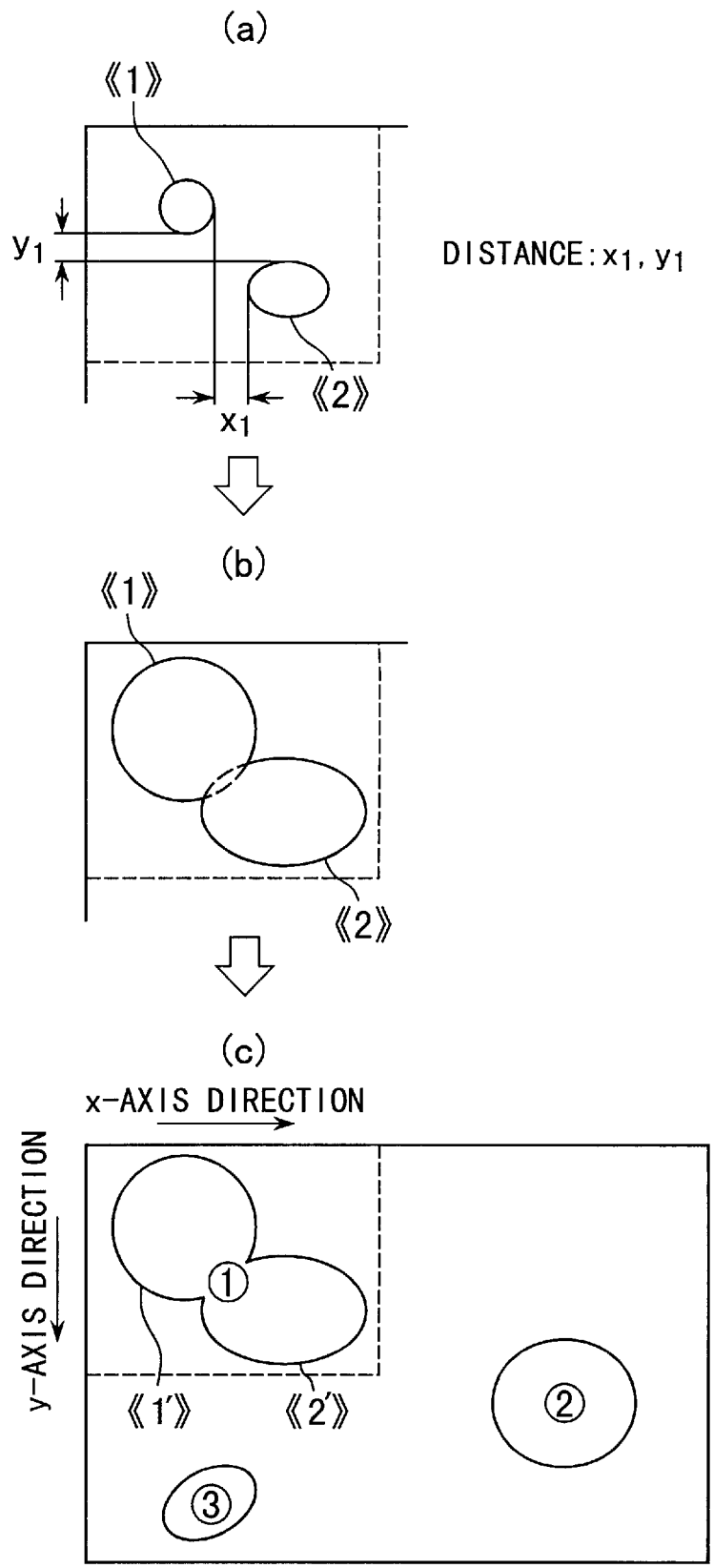
FIG. 5 is a view for explaining the status for extracting and measuring a contour of the medium colony, according to the present invention.

On the stage for feature extraction of bacteria in the step of (e) of FIG. 2, by comparing with the data preliminarily obtained through the procedure mentioned above, those bacteria common in features with the image (Q") of the medium (Q) are extracted. Then, in the colony contour extraction in the step of (f) of FIG. 2, a contour based on the data read is extracted. As shown in FIG. 5(a), the distances (x1) and (y1) between the contours <<1>> and <<2>> are calculated to anticipate the contours <<1'>> and <<2'>> (after a few hours ) of FIG. 5(b) by utilizing the growth degree α. In FIGS. 5(a) and 5(b), the original contours <<1>> and <<2>> of the bacteria are transfigured to the contours <<1'>> and <<2'>> by image developing the result of calculation of the following equations.

$$E = x_1(\alpha_x)$$

$$F = y_1(\alpha_y)$$

In the above equations, $\alpha_x$ is a growth degree component in the x axis direction, $\alpha_y$ is a growth degree component in the y axis direction, E is a growth degree in the x axis direction, and F is a growth degree in the y axis direction. As apparent from FIG. 5(b), the original contours <<1>> and <<2>> are swollen and combined together to become one contour. Then, the number of colonies is counted based on the data obtained by image development as just mentioned. As shown in FIG. 5(c), a labeling is carried out with respect to the contours by scanning them in the x, y axis directions. Then, they are scanned in the y, x axis directions (scanning direction is changed) to establish the numbers (in the illustrated example, the original contours <<1>> and <<2>> are combined together into the single contour <<1'>> and <<2'>> and three colonies ①, ② and ③ appear). Those numbers indicate the number of the colonies. The number of colonies after general cultivating time (24 to 48 hours) is anticipated with reference to the growth degree etc. of accumulated data base. More specifically, the process of growth of the colonies is anticipated based on the data base and then, the number of colonies is anticipated based on both the color density (later described) in the neighborhood of the colonies of the new data and the above-mentioned growth degree. By doing so, the kind of bacteria and the number of colonies are known. Simultaneously or individually of the measurement of the number of colonies counted in the above-described manner, the kind of bacteria is identified.

Figure 6:
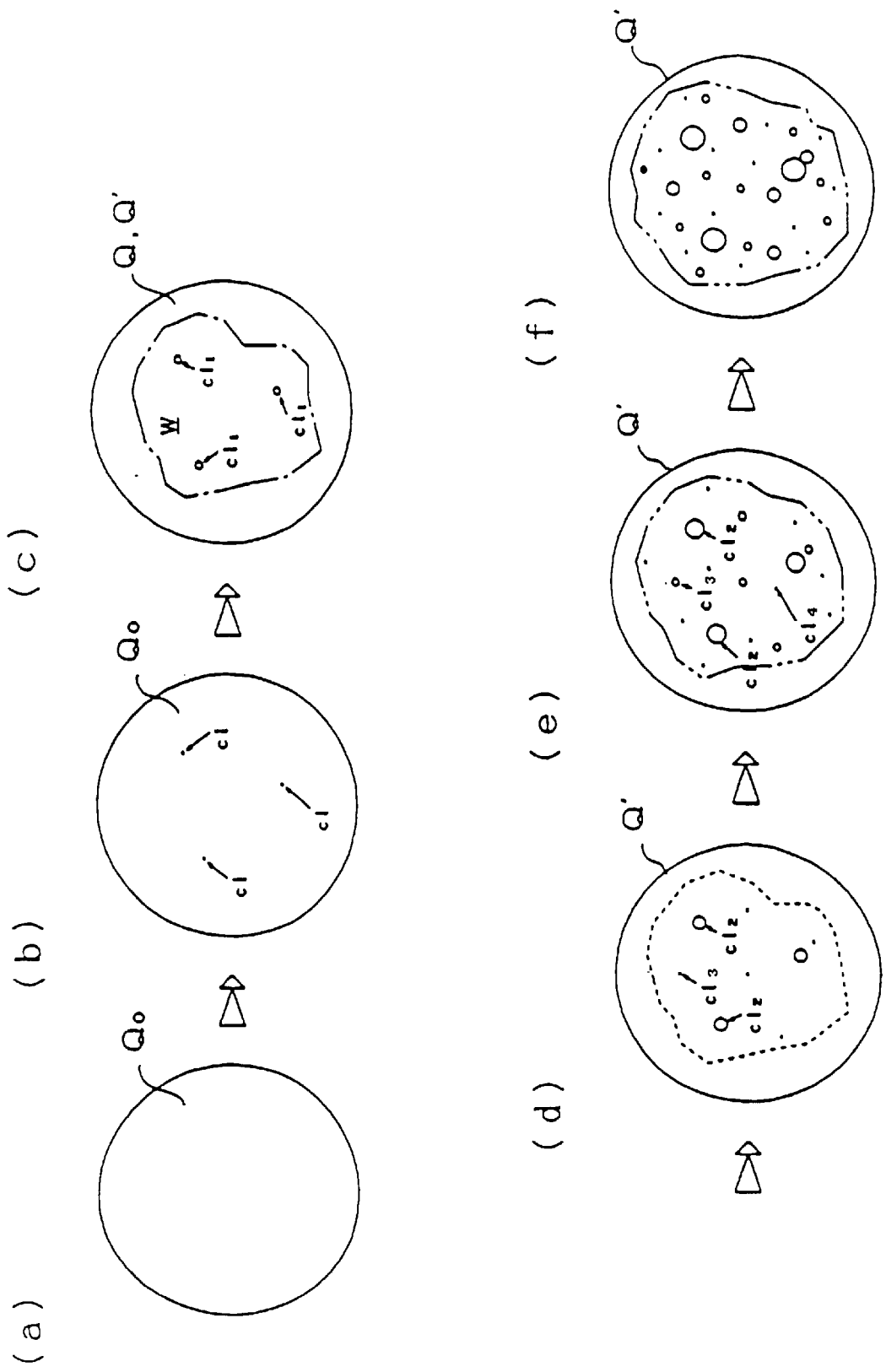
FIG. 6 is a view for explaining the cultivation and anticipation of the growth of the medium, according to the present invention.

FIG. 6(a) shows the surface (culture medium) of a medium ($Q_o$) where bacteria, even present, are not apparent yet. FIG. 6(b) shows the surface under cultivation of the bacteria, where colony (c1) of the bacteria can be seen. FIG. 6(c) shows the surface after the passage of 4 to 6 hours, for example. The cultivating time continues until this time. On this surface, there can be seen not only the colony ($c1_1$) as a result of growth of the colony (c1) but also the change in color in the neighborhood are (W). Thus, an image (Q') of the medium ($Q_o$) is read in the same manner as mentioned above, the kind of bacteria is identified in comparison with the data base (D), and the growth degree, the feature coefficient, etc. are set. Then, the growth anticipation is made by utilizing color, hue, color density, growth degree, feature coefficient, etc. of the neighborhood area (W) of the colony ($c1_1$). FIG. 6(d) shows the surface in the progress of growth of the colonies, where the colony ($c1_2$) as a result of further growth of the colony ($c1_1$) and a generation of a new colony ($c1_3$) can be seen. In FIG. 6(e), the colonies ($c1_2$) and ($c1_3$) are further grown, and in addition, a new colony ($c1_4$) is generated. FIG. 6(f) shows the surface after the passage of 24 hours, for example, where the above-mentioned colonies are further grown and many new colonies are generated.

A further developed microbes inspecting method from the above-mentioned method, according to the present invention, will now be described. An image of a medium obtained from a sample collected from a substance or a solid having microbes or the above-mentioned medium which are subjected to light emitting treatment, dyeing treatment, or the like in accordance with necessity before or after cultivation is separated into the three primary colors, then, chromatic information of histogram, color and hue for each primary color are calculated, and the information thus obtained is compared with integrated data obtained by combining second data of generic information of microbes, etc. with first data of microbes, etc. which are preliminarily accumulated in the same procedure as the above, so that the features specific to microbes are extracted for identification of the kind of the microbes, and then, a state of propagation of the microbes after the passage of a predetermined time is anticipated, thereby a state of propagation of the microbes after the passage of a predetermined time required for cultivation of microbes in the medium can preliminarily be detected.

Examples of methods which can be included in the second data such as the aforementioned generic information of microbes [PCR: random PCR (RAPD), pulse field gel electrophoresis (PFGE)], etc., include the typical cultivating method, oxygen antibody (EIA), immune magnetic beads process, and the like. All or some of the data obtained by expressing the features of the microbes thus obtained in the form of figures are used. In this way, according to the teaching of the present invention, an integrated data obtained by combining second data of generic information of microbes, etc. with first data of microbes, etc. which are preliminarily accumulated in the same procedure as the above, are used and compared with the new medium. That is, when the result of comparison of the first data with the new medium to be inspected reveals that the new medium is the same as a certain bacterium of the first data, the particular data are extracted and at the same time, generic information related thereto is also extracted. Therefore, the bacteria can be correctly identified based on the generic information, thus further enhancing the accuracy of identification of the kind of bacteria.

Figure 7:
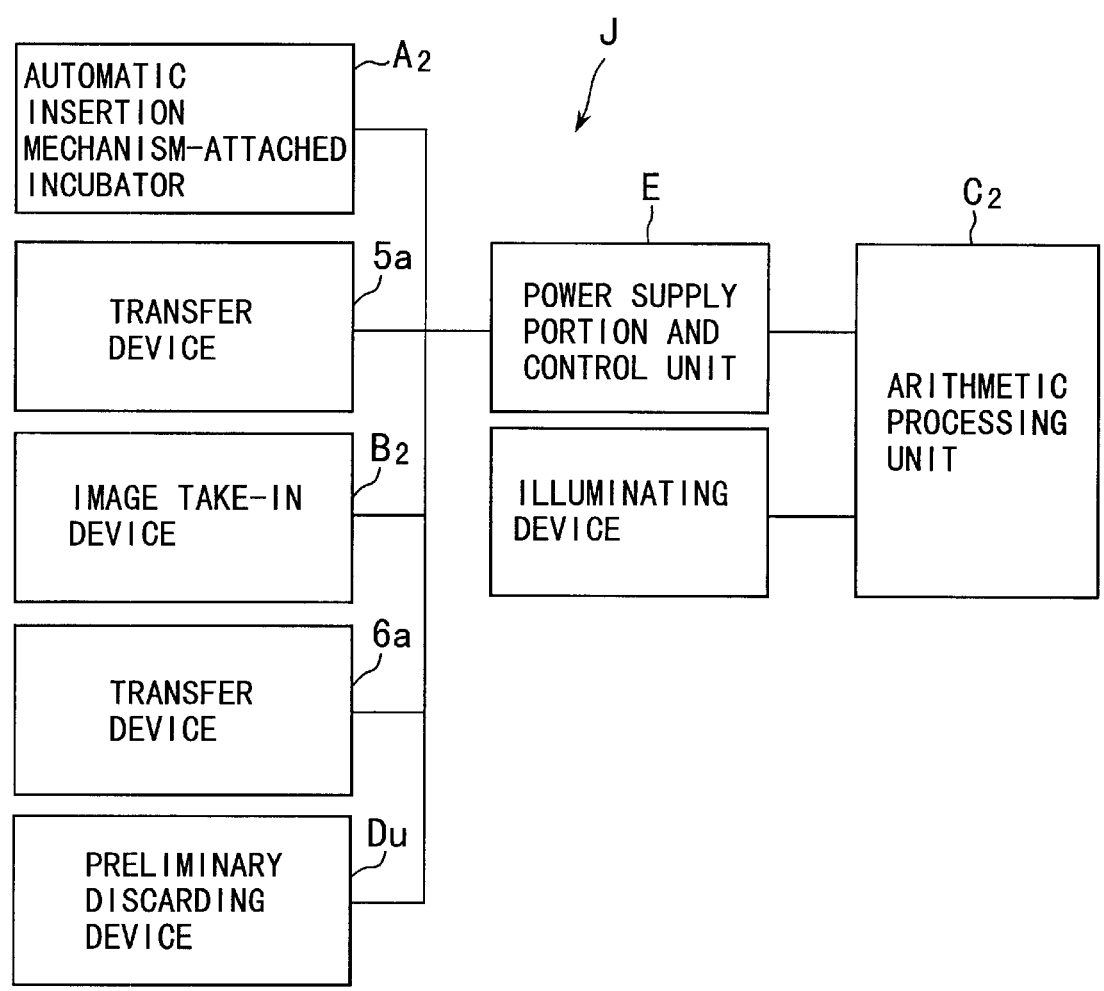
FIG. 7 is a view of a construction showing an apparatus for inspecting microbes, etc., according to the present invention.
Figure 8:
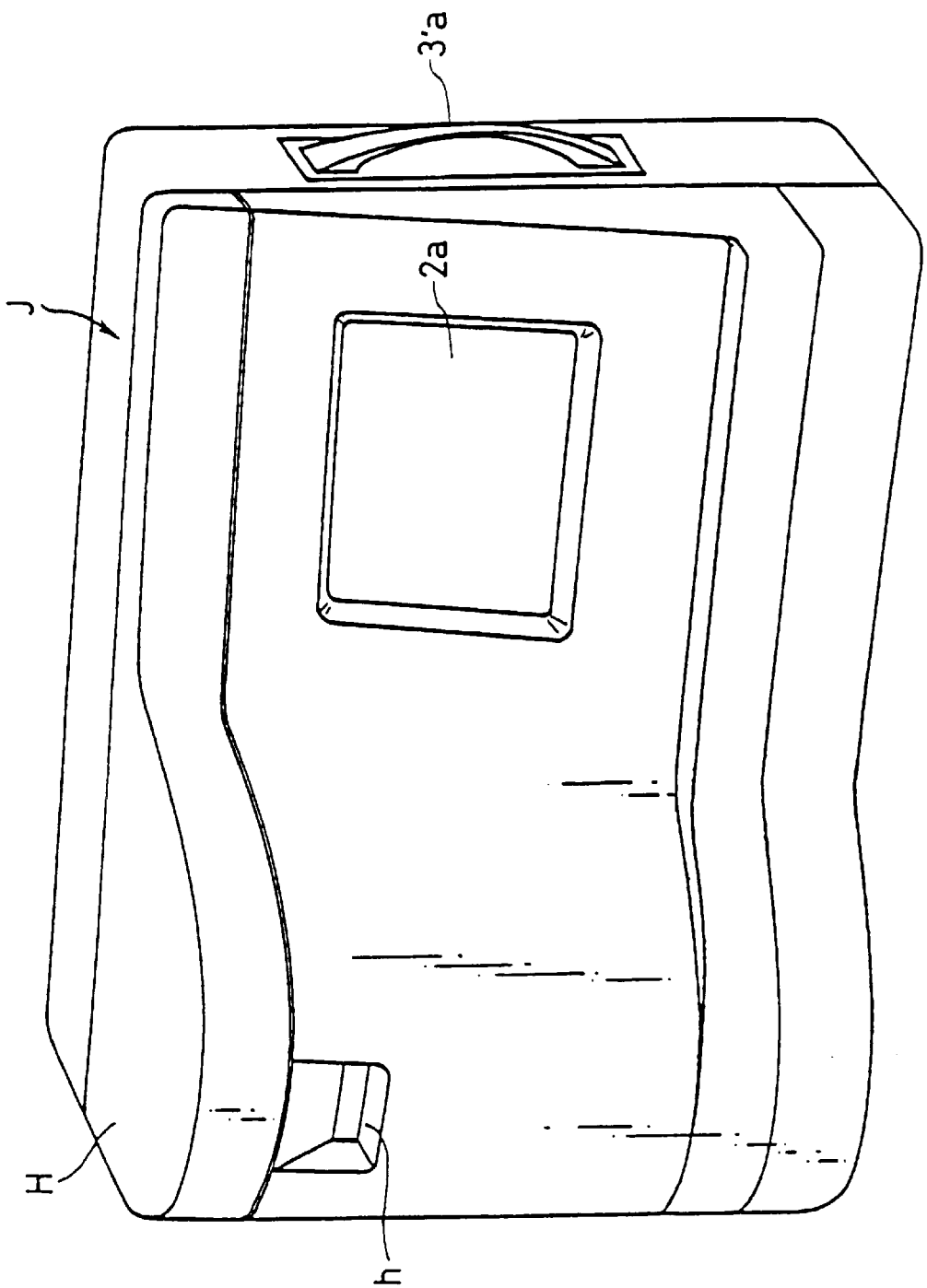
FIG. 8 is an outer appearance view of one embodiment of the apparatus for inspecting microbes, etc., according to the present invention.

FIG. 7 shows an arrangement of such component devices constituting the inspecting apparatus (J) according to one embodiment of the present invention, as a cultivating device [automatic insertion mechanism-attached incubator] ($A_2$), an image take-in device ($B_2$), an arithmetic processing unit ($C_2$) [computer, etc.], a preliminary discarding device (Du), and a power source portion and a control unit (E). FIG. 8 is an outer appearance view of the inspecting apparatus (J) in which those components devices of FIG. 7 are housed, as one group, within the casing (H). The casing (H) of the inspecting apparatus (J) of FIG. 8 has an insertion port (h) formed on a left side of its front surface. Through this insertion port (h), the petri dishes (1a) each containing therein a medium (x) as a culture medium inoculated with bacteria are inserted one by one. The casing also has a monitor screen (2a) formed on a right side of its front surface. The result of inspection, the state of the neighborhood area and the like can be observed in the monitor screen (2a). The casing (H) is provided on a right side of its side surface with a handle (3'a) for taking out a magazine (3a) (as later described) for receiving therein the medium contained petri dishes (1a) which are stacked up 20 pieces each and arranged in four rows. Since formation of colonies is more enhanced when magnetic field and electric field are applied to the medium (x), the inspecting apparatus of FIG. 8 having a unit form of its component devices can more shorten the cultivating time.

Figure 9:
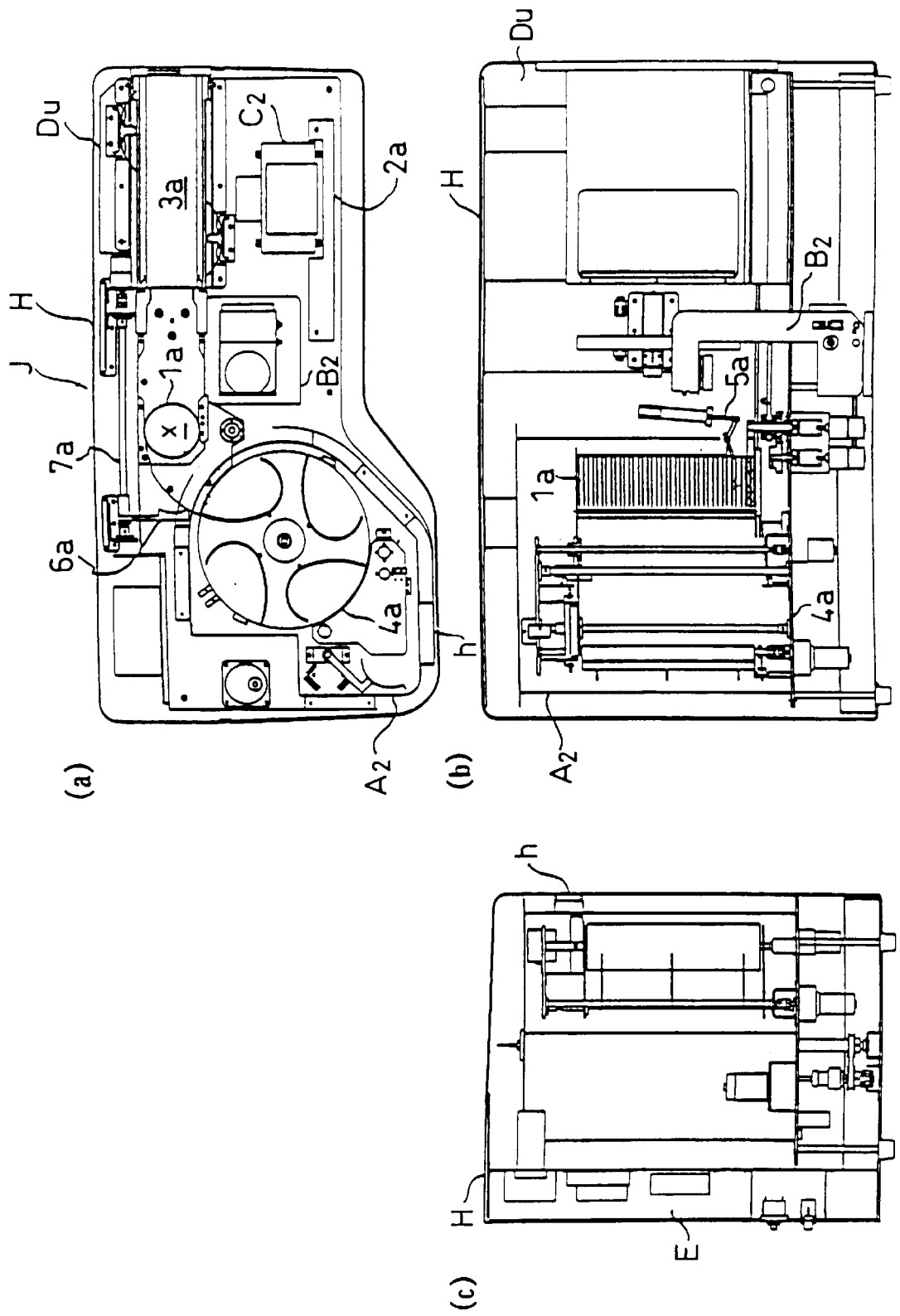
FIG. 9 is a view showing an essential portion of the inside of the apparatus for inspecting microbes, etc., according to the present invention.

FIG. 9(a) is a plan view showing the interior of the casing (H) of FIG. 8. The petri dishes (1a) containing the medium (x) and inserted, one by one, through the insert port (h) are each assigned with an identification mark such as a bar code or the like and vertically stacked up 20 pieces each to form one set such that four sets of medium-contained petri dishes (1a) are arranged within an inner periphery of a table (4a) in the cultivating device ($A_2$). Thus, 80 medium-contained petri dishes (1a) can be received in the cultivating device ($A_2$). The mediums (x) are cultivate for a predetermined time (six hours, for example) within the cultivating device ($A_2$). When the cultivation is finished, the petri dishes (1a) are taken out, one by one, from under the casing (H) by a medium-contained petri dish take-out mechanism (5a) (see FIG. 7). After a cover of each petri dish (1a) is opened, the medium (x) is transmitted to an image take-in device ($B_2$) [CCD camera or the like] so as to be photographed. Then, the date of the photograph are taken into the arithmetic processing unit ($C_2$). After photographing, the medium-contained petri dish (1a) is closed its cover and then transmitted to a magazine (3a) located backwardly, by a medium-contained petri dish transfer arm (6a) through guidance of a shuttle mechanism (7a). In the magazine (3a), the medium-contained petri dishes (1a) are stacked up 20 pieces each and arranged in four rows for accumulation. Then, they are sterilized by a preliminary discarding device (Du) [sterilizing lamp or the like]. Thereafter, the magazine (3a) is taken out of the casing (H).

It is also an interesting alternative that instead of providing the preliminary discarding device (Du) within the casing (H), the medium-contained petri dish (1a) is sterilized after it is taken out of the casing (H). FIG. 9(b) showing the front side of the interior of FIG. 9(a) but the arithmetic processing unit ($C_2$) portion is omitted. FIG. 9(c) is a side view likewise showing the interior of FIG. 9(a). It is also accepted that a device for sterilizing device such as, for example, a microwave or the like is installed within the casing (H). In this embodiment, a culture medium inoculated with bacteria is employed. It should be noted, however, that the present invention is by no means limited to this embodiment and that other mediums may selectively be employed depending on the kind and form of the medium (x). It may also be designed such that an alarm lamp, a buzzer or the like are actuated when it detects that particular bacteria are increased more than a predetermined level. It is also accepted that a device for measuring the state of temperature, moisture, dust, etc, in space is separately installed within a chamber or else where the housing (H) is disposed, so that information obtained by it is taken into the arithmetic processing unit ($C_2$) for management of environment.

Figure 10:
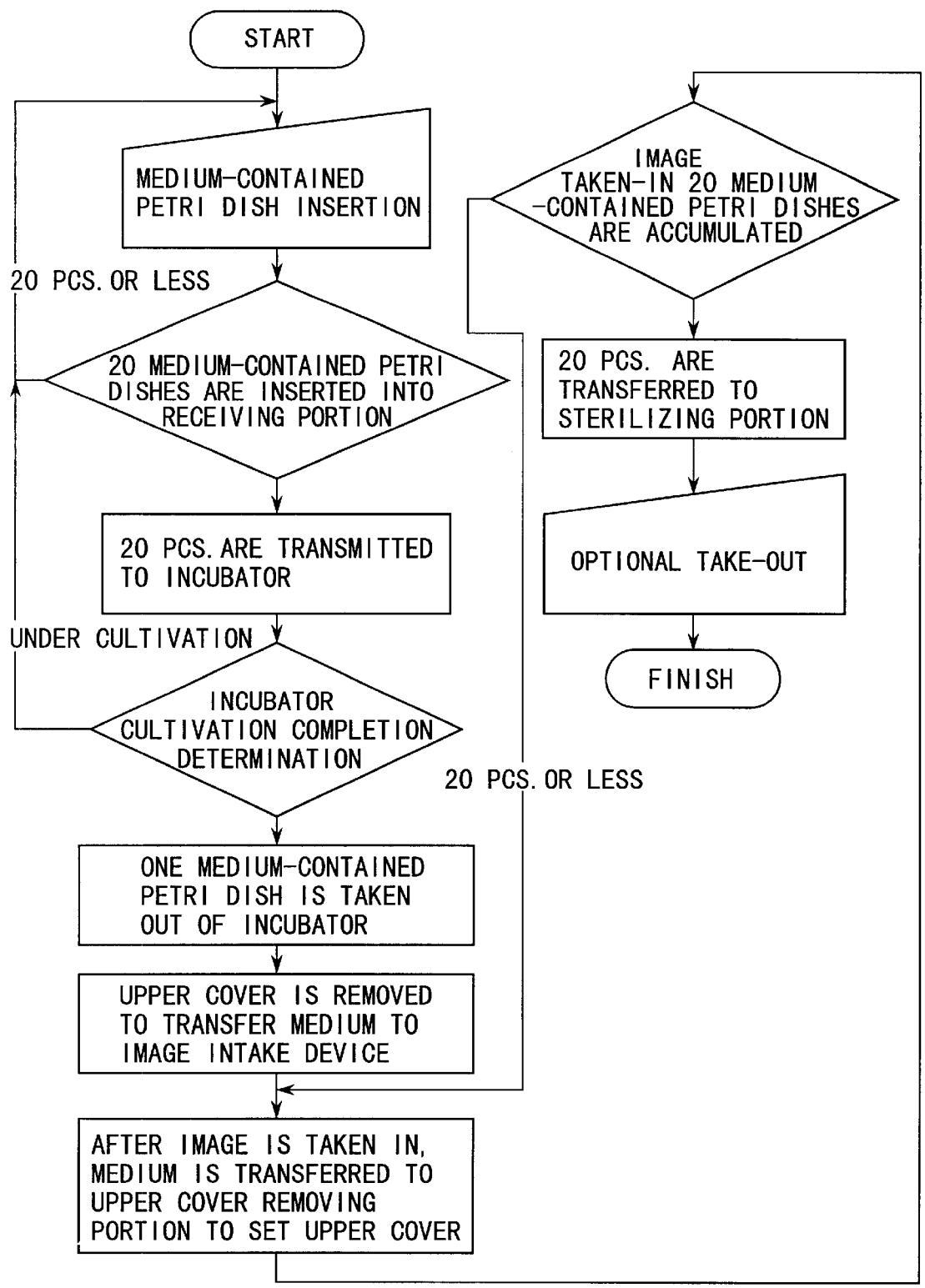
FIG. 10 is a flowchart for explaining the processes of procedure, starting from insertion of the medium and ending in removal of the medium, according to the present invention.

FIG. 10 is a flowchart showing the procedure including the steps of insertion of medium-contained petri dish (1a), accumulation of the medium-contained petri dish (1a) in the cultivating device ($A_2$), transfer of the same, determination of cultivation completion, take-out of such petri dish (1a), transfer of the medium to the image take-in device ($B_2$) after an upper cover of the petri dish (1a) is removed, setting the upper cover after an image is taken in, accumulation, and transfer to the preliminary discarding device (Du), take-out, and finish.

An illuminating mechanism employed for photographing the medium (x) will now be described. For photographing the medium (x), it is indispensable that the medium (x) is clearly lighted. For this purpose, it is customary that the medium is illuminated from top. This method of illumination is effective when the medium is thin. But since light tends to transmit therethrough, it is sometimes difficult to obtain a detailed image. In consideration of this fact, according to the present invention, there is a provision of an illumination mechanism which is variable, where necessary, in intensity of illumination at an upper and a lower surface. This illumination mechanism projects illumination light towards the medium (x) by sandwiching it. The illuminating device has a feedback function capable of automatically adjusting the intensity of illumination depending on the medium (x). By this arrangement, a reflecting light and a transmissible light are brought to the medium (x) so that an image of the detailed portion can be photographed.

Figure 11:
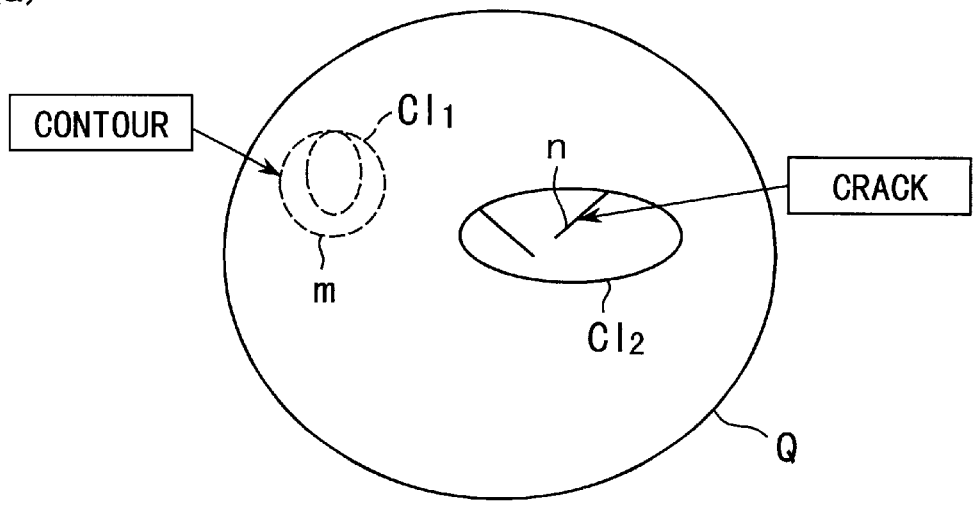
FIG. 11 is a view for explaining the extraction of an image of the medium colony and a state of illumination of crack.
Figure 11:
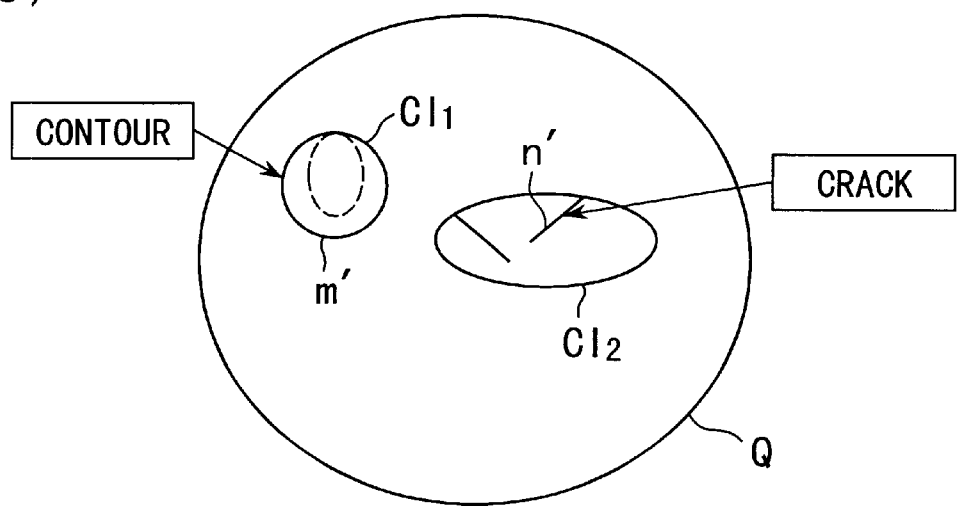

This procedure will be described in more detail with reference to FIGS. 11(a) and 11(b). FIG. 11(a) shows one image (Q) of the medium where a contour m of the colony ($c1_1$) and a crack formed in the colony ($c1_2$) are also shown. Description will be made here presuming that an illumination light 1 is projected from only one side. Although the contour m of the colony ($c1_1$) is somehow recognizable (detectable), it is necessary in some cases to adjust the intensity of illumination in order to obtain a more accurate contour m. It is more difficult to obtain a clear image of crack of the colony ($c1_2$) with the same intensity of illumination as the intensity of illumination for detecting the contour m. Further, in order to determine the contour M, it is necessary to increase the intensity of illumination. However, if the intensity of illumination is increased, determination of the crack n becomes difficult in some cases. According to the present invention, by transmitting an illumination light from a lower surface, a more detailed contour m' can be obtained as shown in FIG. 5(b). Also, by varying the intensity of illumination of the illuminating device depending on the medium (x), a detailed portion of the crack n' can be obtained.

Figure 12:
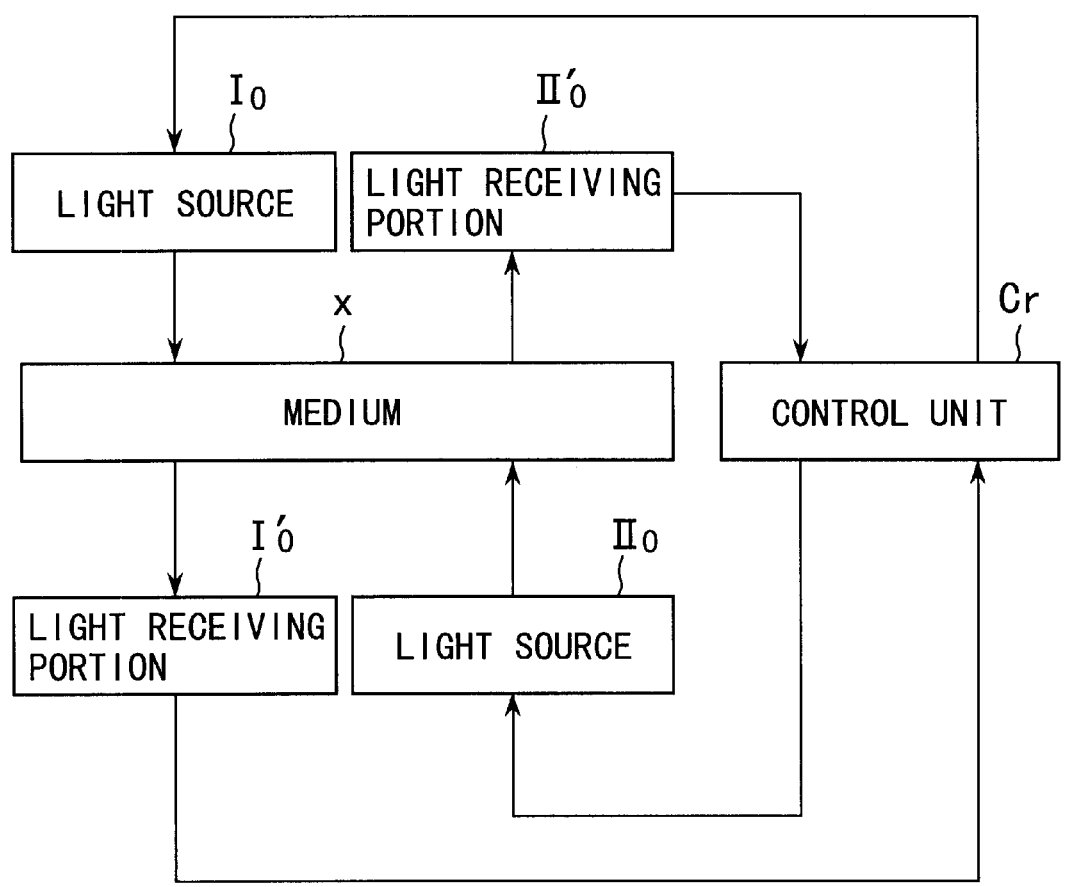
FIG. 12 is a view showing an arrangement of a light source and a light receiving portion for the medium and a control device, according to the present invention.

FIG. 12 shows how two light sources ($I_0$), ($II_0$) and two light receiving portions ($I'_0$), ($II_0'$) are arranged with respect to the medium (x) and positional relationship of a control unit (Cr) with the light sources ($I_0$), ($II_0$) and the light receiving portions ($I'_0$), ($II'_0$). In this way, there are employed in this embodiment two kinds of light sources. Of the two light sources ($I_0$), ($II_0$), the light source ($I_0$) serves as a reference light source and the other light source ($II_0$) emits light of full colors. The light source ($I_0$) is disposed in such a manner as to surround the medium (x). In operation, this light source ($I_0$) projects a reference light, the light reflected by the medium (x) is detected by the light receiving portion ($I'_0$), and a signal is sent to the control unit (Cr). The control unit (Cr) compares the receiving signal with the projecting signal and sends an optimum signal to the light source ($I_0$) The same operation is also made with respect to the other light source ($II_0$). In this way, the features of the medium (x) is more precisely recognized by using two kinds of light sources. The number of such light sources may be increased. It is also effective that the intensity of illumination is designed to be variable.

Figure 13:
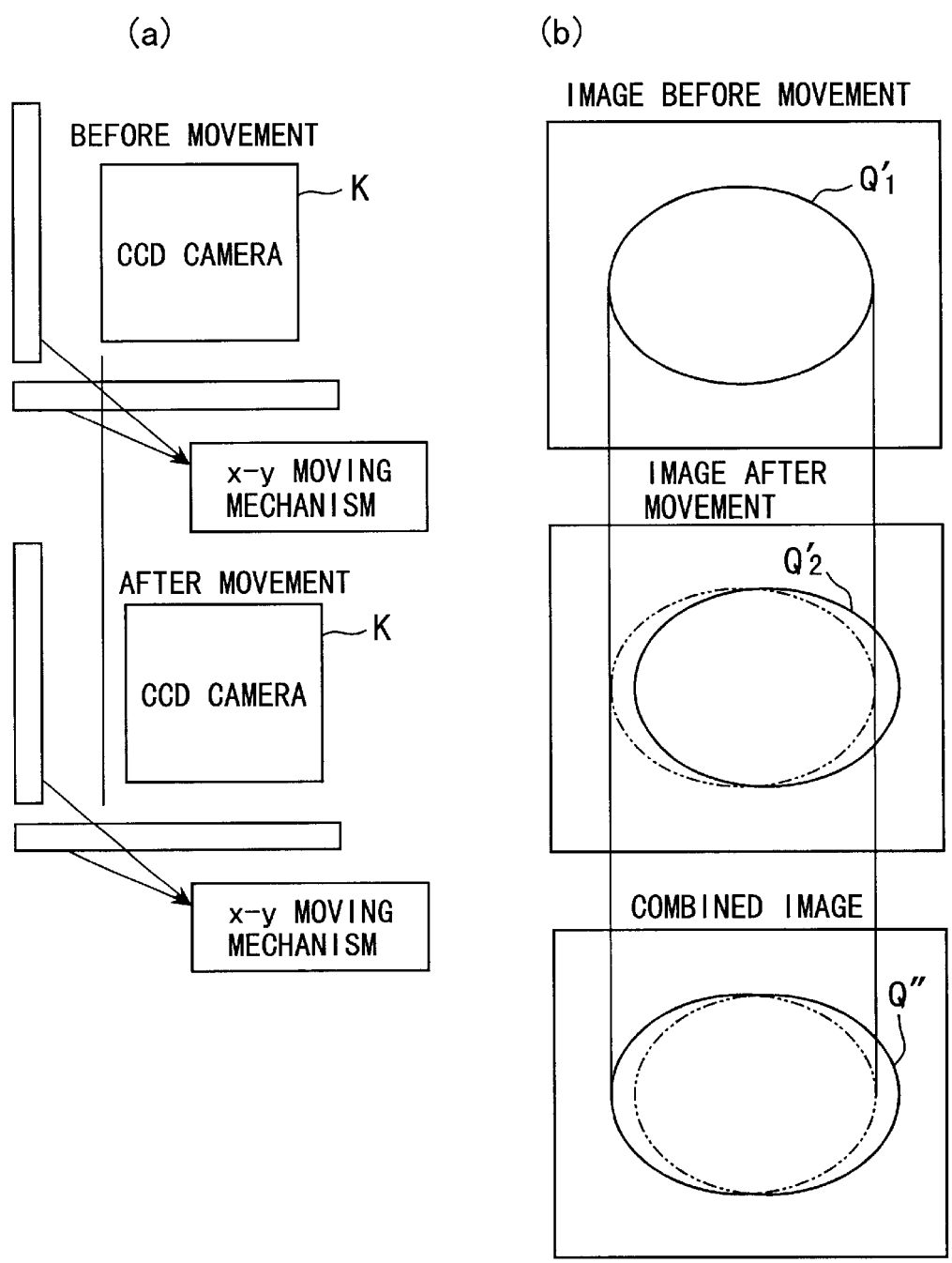
FIG. 13 is an explanatory view of a photographing device for the medium, according to the present invention.

The CCD camera is slightly moved. FIG. 13 is a view showing how the image is moved before and after the movement of the CCD camera (K). That is, the CCD camera (K) is mounted on a mechanism capable of movement in both the X-axis direction and the Y-axis direction, and as shown in FIG. 13(b), an image ($Q'_1$) before movement and an image ($Q'_2$) after movement are caught, and a result thereof is interpolation-operated to form an image (Q''), so that dissolution is enhanced. The image N obtained by this method is obtained by dividing the image $N_0$ before movement and the image $N_1$, after movement into two. The same result can also be achieved by using, where necessary, a mechanism for moving the medium (x) without moving the CCD camera (K).

Figure 14:
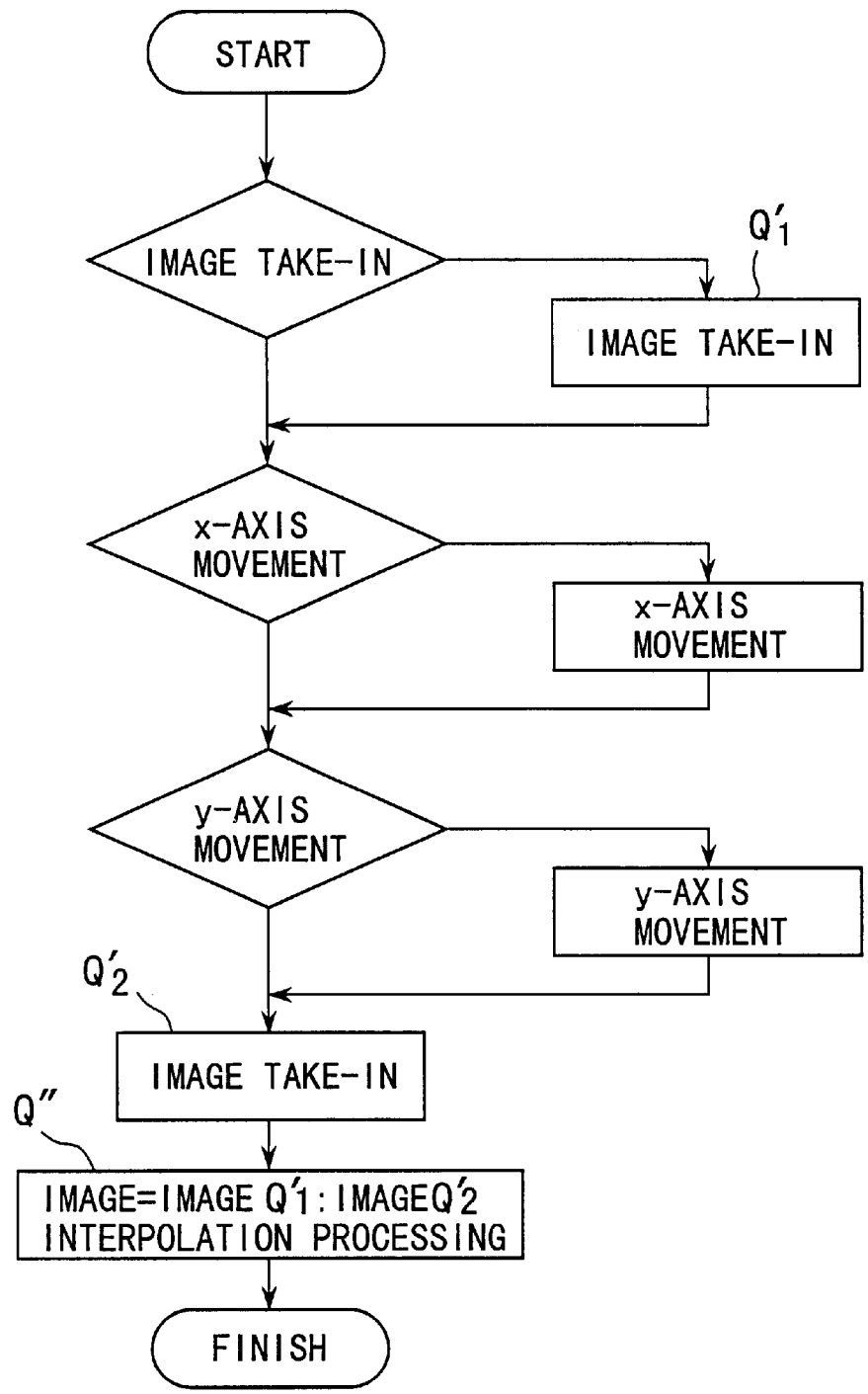
FIG. 14 is a flowchart of the procedure from the start of the take-in operation of an image of the medium till the end, according to the present invention.

FIG. 14 is a flowchart showing the whole procedure including the steps of take-in of the image ($Q'_1$), the X- and Y-axis movement, take-in of the image ($Q'_2$), obtaining an image (Q") through interpolation processing and finish.

It is also accepted that a light emitting material, capable of emitting light when a ray of light such as a near ultraviolet ray is irradiated thereto is mixed with the material forming the petri dish itself of the medium-contained petri dish (1a), so that an image is read while emitting a fluorescent light. By doing so, determination accuracy can be enhanced.

INDUSTRIAL APPLICABILITY

For inspecting a collected medium during the course of processing food, it is important to know how rapidly bacteria propagate when poisoning bacteria are detected in the medium. Greatly propagated bacteria can, of course, be the cause of food poisoning. However, it usually takes a certain time for inspecting microbes, and the time required is different depending on the kind of bacteria. The required time is also changed even for the same kind of bacteria depending on conditions of outer circumstance. With a hope to cope with such situation, the present invention makes it possible to preliminarily identify the kind of bacteria and anticipate the growing speed of the bacteria in the medium in a short time. According to the present invention, the state of the identified bacteria after the passage of a predetermined time can be known in advance in a short time.

In the present invention, an image of the bacteria cultivated in a short time (about 5 to 6 hours) is separated into the three primary colors, for example, then, histogram, color and hue are calculated for each color to establish a growth coefficient for anticipating the growth of colonies of bacteria and a feature coefficient for determining the features specific to each microbe. Then, the same is compared with the data which are preliminarily calculated in the same manner as mentioned above and accumulated. In accordance with necessity, integrated data containing generic information are searched for comparison. In doing so, the kind of bacteria is identified. Further, by utilizing the growth coefficient, etc., a propagating state of the bacteria after the passage of time (24, 48 hours, for example) generally required for cultivating the bacteria is anticipated, thereby the propagating state of bacteria after the passage of a predetermined time can easily be known in a short time. The present invention provides such a method and an apparatus capable of determining microbes with high precision. Also, according to the present invention, devices for accurately photographing the microbes and inspecting the medium are housed, as one group, in a casing, so that the medium can be determined automatically and the result of the inspection can be accumulated efficiently. In addition, the medium can easily be sterilized. The apparatus thus constructed can be installed in various inspecting organizations, and other entities. With this apparatus, the target medium can automatically be determined without any knowledge of the medium, and the result is accumulated for the future inspection. Moreover, by sterilizing the medium in a predetermined manner, the medium can be discarded safely. In this way, anybody can correctly inspect without a need of specialists.

That is, according to the present invention, without a need of hard training, anybody can easily and efficiently inspect the propagating state of microbes, etc. in advance.

According to the present invention, the actual state of microbes can be inspected by only cultivating them in a short time (about 24 or 48 hours are conventionally required as previously mentioned). By accumulating and comparing the data of microbes, the kind of the microbes can correctly be known by identifying the microbes and anticipating the state of generation. Moreover, by increasing and additionally accumulating the data to be compared, the inspection accuracy can be more enhanced.

The present invention can be of great help for perfect safety management of food and also be extremely useful for fulfilling the requirements of PL law, HACCP (Hazard Analysis Critical Control Point; or GMP (Good Manufacturing Practice) which were recently widely known. In addition, the present invention can be applied not only to the field of food including drinking water but also to the field of clinic, sanitary, agriculture, earth, sea water, drain and other water, wood, air and many others where microbes can propagate.

What is claimed is:

1. A method for inspecting a sample, said method comprising:
   stacking vertically sample petri dishes in a cultivating device;
   cultivating the sample petri dishes for a predetermined period of time;
   removing the sample petri dishes, one by one from the cultivating device;
   opening a cover of one of the sample petri dishes removed from the cultivating device;
   taking an image of one of the sample petri dishes possibly containing microbes using an imaging device;
   covering the one sample petri dish imaged;
   stacking the covered sample petri dishes imaged;
   separating the image into the three primary colors;
   analyzing the separated primary colors for chromatic information comprising histogram, color and hue data;
   comparing the chromatic information with data previously collected corresponding to known microbes after respective analysis of separated primary colors;
   identifying a microbe in the sample which matches the data of known microbes; and
   determining a state of propagation of the identified microbe by extrapolating the previously known growth rate of the now identified microbe to a desired period of time which is greater than the predetermined period of time using a processor operatively associated with the imaging device;
   wherein said cultivating device, the imaging device, and the processor, and a preliminary discarding device are housed, as a unit, in a casing having an inlet port for inserting, one by one, petri dishes containing said sample therethrough such that said sample petri dishes inserted through said inlet port are vertically stacked up on a round table rotatable within said casing, said sample petri dishes are removable, one by one, from under said casing by a sample petri dish removing mechanism, and after the passage of a predetermined cultivating time, after opening a cover, said sample petri dishes are transferable to said imaging device, and, after photographing the sample, data thereof is transferable to said processor, and, after closing said cover, said sample petri dishes photographed are transferable to a magazine by a sample petri dish feed arm so that a predetermined number of said sample petri dishes are stacked up for accumulation.

2. The method of claim 1, wherein, prior to taking an image of one of the sample petri dishes, the one sample petri dish is subjected to dye treatment either prior to or after cultivation.

3. The method of claim 1, wherein, prior to taking an image of the sample petri dish, the one sample petri dish is subjected to illumination treatment either prior to or after cultivation.

4. A method for inspecting a medium, said method comprising:

stacking vertically sample petri dishes in a cultivating device;

cultivating the sample petri dishes for a predetermined period of time;

removing the sample petri dishes, one by one from the cultivating device;

opening a cover of one of the sample petri dishes removed from the cultivating device;

taking an image of one of the sample petri dishes possibly containing microbes using an imaging device;

covering the one sample petri dish imaged;

stacking the covered sample petri dishes imaged;

separating the image into the three primary colors;

analyzing the separated primary colors for chromatic information comprising histogram, color and hue data;

comparing the chromatic information of the sample with integrated data obtained by combining:
(i) a first set of data containing chromatic information corresponding to known microbes previously collected using this method of analyzing separated primary colors of respective known microbes, and
(ii) a second set of data corresponding to generic information of the known microbes;

identifying a microbe in the sample which matches the data of known microbes; and determining a state of propagation of the identified microbe by extrapolating the known growth rate of the identified microbe to a desired period of time which is greater than the predetermined period of time using a processor operatively associated with the imaging device;

wherein said cultivating device, the imaging device, and the processor, and a preliminary discarding device are housed, as a unit, in a casing having an inlet port for inserting, one by one, petri dishes containing said sample therethrough such that said sample petri dishes inserted through said inlet port are vertically stacked up on a round table rotatable within said casing, said sample petri dishes are removable, one by one, from under said casing by a sample petri dish removing mechanism, and after the passage of a predetermined cultivating time, after opening a cover, said sample petri dishes are transferable to said imaging device, and, after photographing the sample, data thereof is transferable to said processor, and, after closing said cover, said sample petri dishes photographed are transferable to a magazine by a sample petri dish feed arm so that a predetermined number of said sample petri dishes are stacked up for accumulation.

5. The method of claim 4, wherein, prior to taking an image of the one sample petri dish, the one sample petri dish is subjected to dye treatment either prior to or after cultivation.

6. The method of claim 4, wherein, prior to taking an image of the sample petri dish, the one sample petri dish is subjected to illumination treatment either prior to or after cultivation.

7. An apparatus for inspecting microbes, said apparatus comprising:

a cultivating device;

an imaging device; and a processor, said processor operatively associated with said imaging device for:
processing an image of a sample contained in said cultivating device;
separating the image into the three primary colors;
analyzing the separated primary colors for chromatic information comprising histogram, color and hue data;
comparing the chromatic information with data previously collected corresponding to known microbes after respective analysis of separated primary colors;
identifying a microbe in the sample which matches the data of known microbes; and
determining a state of propagation of the identified microbe by extrapolating the known growth rate of the identified microbe to a desired period of time which is greater than a predetermined period of time; and a casing having an inlet port for inserting, one by one, petri dishes containing said sample therethrough such that said sample petri dishes inserted through said inlet port are vertically stacked up on a round table rotatable within said casing, said sample petri dishes are removable, one by one, from under said casing by a sample petri dish removing mechanism, and after the passage of a predetermined cultivating time, after opening a cover, said sample petri dishes are transferable to said imaging device, and, after photographing the sample, data thereof is transferable to said processor, and, after closing said cover, said sample petri dishes photographed are transferable to a magazine by a sample petri dish feed arm so that a predetermined number of said sample petri dishes are stacked up for accumulation, wherein said casing houses, as a unit, the cultivating device, the imaging device, the processor and a preliminary discarding device.

8. The apparatus of claim 7, wherein said casing is provided with a monitor screen.

9. The apparatus of claim 7, further comprising a device for sterilizing said sample.

10. The apparatus of claim 7, further comprising one of an alarm lamp or a buzzer which is actuated when detecting specific bacteria are more propagated than a predetermined level.

11. The apparatus of claim 7, further comprising a monitor associated with the cultivating device and capable of measuring temperature, moisture and dust in a space of said cultivating device, thereby data obtained by said monitor are sent to said processor for managing said space.

12. An apparatus for inspecting microbes, said apparatus comprising:

a cultivating device;

an imaging device;

a processor, said processor operatively associated with said imaging device for:
processing an image of a sample contained in said cultivating device;
separating the image into the three primary colors;
analyzing the separated primary colors for chromatic information comprising histogram, color and hue data;
comparing the chromatic information with
(a) data previously collected corresponding to known microbes or (b) integrated data obtained by combining
  (i) a first set of data containing chromatic information corresponding to known microbes previously collected after analyzing the respective separated primary colors of the known microbes, and
  (ii) a second set of data corresponding to generic information of the known microbes;
identifying a microbe in the sample which matches the data of known microbes; and
determining a state of propagation of the identified microbe by extrapolating the known growth rate of the identified microbe to a desired period of time which is greater than a predetermined period of time; and
a casing having an inlet port for inserting, one by one, petri dishes containing said sample therethrough such that said sample petri dishes inserted through said inlet port are vertically stacked up on a round table rotatable within said casing, said sample petri dishes are removable, one by one, from under said casing by a sample petri dish removing mechanism, and after the passage of a predetermined cultivating time, after opening a cover, said sample petri dishes are transferable to said imaging device, and, after photographing the sample, data thereof is transferable to said processor, and, after closing said cover, said sample petri dishes photographed are transferable to a magazine by a sample petri dish feed arm so that a predetermined number of said sample petri dishes are stacked up for accumulation, wherein said casing houses, as a unit, the cultivating device, the imaging device, the processor and a preliminary discarding device.

13. The apparatus of claim 7, wherein the data of known microbes comprises bacteria name, feature coefficient of red, green and blue histogram, hue value and generic information of microbes.

14. The apparatus of claim 7, further comprising an illumination device having a light source for emitting light for photographing the sample and corresponding to at least one light source.

15. The apparatus of claim 7, wherein said imaging device comprises a camera and a device for manipulating the sample.

* * * * *